United States Patent [19]

Richarz et al.

[11] 4,297,493

[45] Oct. 27, 1981

[54] MANUFACTURE OF 4-AMINO-5-CHLORO-1-PHENYLPYRIDAZ-6-ONE USING AQUEOUS PHENOL-4-SULFONIC ACID

[75] Inventors: Winfried Richarz; Helmut Froehlich; Harald Schroeder, all of Ludwigshafen, Fed. Rep. of Germany

[73] Assignee: BASF Aktiengesellschaft, Fed. Rep. of Germany

[21] Appl. No.: 185,403

[22] Filed: Sep. 8, 1980

[30] Foreign Application Priority Data

Sep. 15, 1979 [DE] Fed. Rep. of Germany ....... 2937421

[51] Int. Cl.³ ............................................ C07D 237/14
[52] U.S. Cl. .................................................... 544/241
[58] Field of Search ........................................ 544/241

[56] References Cited

U.S. PATENT DOCUMENTS 4,237,287  12/1980  Motta ................................. 544/241

FOREIGN PATENT DOCUMENTS 1620186  2/1970  Fed. Rep. of Germany .
2925110  1/1980  Fed. Rep. of Germany .
116615  12/1975  German Democratic Rep. .
124918  3/1977  German Democratic Rep. .
131172  7/1977  German Democratic Rep. .
871674  6/1961  United Kingdom .

*Primary Examiner*—Mark L. Berch
*Attorney, Agent, or Firm*—Keil & Witherspoon

[57] ABSTRACT

The manufacture of substantially pure 4-amino-5-chloro-1-phenylpyridaz-6-one by reaction of 4,5-dichloro-1-phenylpyridaz-6-one with ammonia in the presence of phenol-4-sulfonic acid.

2 Claims, No Drawings

MANUFACTURE OF 4-AMINO-5-CHLORO-1-PHENYLPYRIDAZ-6-ONE USING AQUEOUS PHENOL-4-SULFONIC ACID

The present invention relates to a process for the manufacture of substantially pure 4-amino-5-chloro-1-phenylpyridaz-6-one by reaction of 4,5-dichloro-1-phenylpyridaz-6-one with ammonia in the presence of phenol-4-sulfonic acid.

The use of 4-amino-5-chloro-1-phenylpyridaz-6-one as a herbicide, especially for the selective control of weeds in sugarbeets, has been disclosed. The compound is manufactured in accordance with British 871,674 by reaction of 4,5-dichloro-1-phenylpyridaz-6-one with aqueous ammonia at superatmospheric pressure and elevated temperatures. A mixture is obtained of which about 80% (wt %) is 4-amino-5-chloro-1-phenylpyridaz-6-one and about 20% is the isomeric 5-amino-4-chloro-1-phenylpyridaz-6-one, which is not such a good herbicide. In order to manufacture crop protection agents containing as much biologically active ingredient as possible, technical-grade active ingredients of the maximum obtainable purity are required. German Laid-Open Application DE-OS No. 1,620,186 discloses the substantial removal of the undesired isomeric compound from the mixture obtained on manufacture by extraction with nonpolar solvents from the group of aromatic and hydroaromatic hydrocarbons.

It has further been disclosed to carry out the reaction of the 4,5-dichlorophenylpyridazone with ammonia in organic solvents, a product of high purity being obtained (German Democratic Republic DD No. 131,172). However, the use of organic solvents is a drawback.

We have now found that 4-amino-5-chloro-1-phenylpyridaz-6-one is readily obtained in excellent yields and high purity when 4,5-dichloro-1-phenylpyridaz-6-one is reacted with an aqueous solutiion of ammonia at from 20° to 200° C. and from 1 to 20 bars in the presence of phenol-4-sulfonic acid.

The process according to the invention has two essential advantages. The first is that, as a result of the use of water as reaction medium, the process is exceedingly simple and therefore economical, because the water-insoluble end product can be separated from the reaction mixture by simple suction filtration; at the same time, the readily water-soluble ammonium salt of phenol-4-sulfonic acid is separated from the end product. The second advantage is that the phenol-4-sulfonic acid influences the isomer ratio during the reaction direct, whereas in the prior art processes the undesired isomeric compound is formed and is removed by employing organic solvents.

In contrast to these prior art processes, the process according to the invention gives, much more simply and economically, the desired 4-aminopyridazone derivative in about 90% yield and 95 to 99% purity.

The reaction may be carried out for instance as follows. 4,5-Dichloro-1-phenylpyridaz-6-one, aqueous ammonia solution and phenol-4-sulfonic acid are introduced into a pressure vessel, the vessel is closed and the mixture is heated to the desired reaction temperature and kept at this temperature for several hours. Advantageously, the reaction components are mixed, for example by stirring. Upon completion of the reaction the reaction mixture is cooled, and the solid is filtered off, washed with water and dried. The use of a 5- to 20-fold molar excess of ammonia, with reference to the 4,5-dichloro compound, and of a 5 to 30% (wt %) strength aqueous ammonia solution has proved to be advantageous. In the reaction with ammonia, the phenol-4-sulfonic acid is in the form of its ammonium salt. The term "phenol-4-sulfonic acid" should, therefore, for the purposes of the invention, also be taken to mean its ammonium salt.

The reaction is carried out at from 20° to 200° C., preferably at least 80° C., advantageously at from 100° to 150° C., and particularly at from 110° to 130° C.

Expediently, the process is carried out in the presence of from 1 to 100 mole% of phenol-4-sulfonic acid, based on the 4,5-dichloro compound, preferably at least 10 mole%, advantageously from 20 to 70 mole%, and especially from 30 to 50 mole%.

The reaction is effected at superatmospheric pressure (1 bar to 50 bars), preferably at from 3 to 10 bars, and especially at the autogenous pressure in the closed reaction vessel when the reaction temperature is reached. It is also possible to increase the pressure in the closed vessel during the reaction by pressuring ammonia in. Some of the ammonia thus introduced dissolves in the aqueous ammonia solution.

The process according to the invention is non-polluting, because the mother liquor obtained on separation of the reaction product can, if desired after the addition of ammonia, aqueous ammonia solution or phenol-4-sulfonic acid, be employed again for reaction with further 4,5-dichloro compound. The mother liquor may therefore be recycled in whole or in part.

The following examples illustrate the simplicity and reliability of the process according to the invention.

EXAMPLE 1

85 parts by volume of 15% (wt %) strength aqueous ammonia, 12.05 parts by weight of 4,5-dichloro-1-phenylpyridaz-6-one and 6.2 parts by weight of a 70% strength aqueous solution of phenol-4-sulfonic acid (parts by volume bearing the same relationship to parts by weight as the liter to the kilogram) are introduced into a jacketed pressure vessel having a capacity of 300 parts by volume. The reaction mixture is heated to 130° C. while stirring and kept for 4 hours at this temperature, while still stirring. The autogenous pressure which is hereupon generated is 6 bars. The reaction mixture is then allowed to cool to room temperature (20° C.) and the mother liquor is completely filtered off. The solid reaction product is washed with water and dried in vacuo at 100° C. There is obtained 9.8 parts by weight (89% of theory) of 4-amino-5-chloro-1-phenylpyridaz-6-one of melting point 205°–206° C. The amount of 5-amino-4-chloro-1-phenylpyridaz-6-one is determined gas-chromatographically and found to be 1%, and the amount of 4-amino derivative 99%.

EXAMPLE 2

The mother liquor separated in Example 1, 12.05 parts by weight of 4,5-dichloro-1-phenylpyridaz-6-one and 15 parts by volume of 15% strength aqueous ammonia are mixed, and kept, as described in Example 1, at 130° C. for 6 hours. After working up there is obtained 10.1 parts by weight (91% of theory) of 4-amino-5-chloro-1-phenylpyridaz-6-one of melting point 202°–204° C. The amount of 5-amino-4-chloro-1-phenylpyridaz-6-one was determined gas-chromatographically and found to be 2–3%, and the amount of 4-amino derivative 96%.

We claim:

1. A process for the manufacture of substantially pure 4-amino-5-chloro-1-phenylpyridaz-6-one by reaction of 4,5-dichloro-1-phenylpyridaz-6-one with ammonia, wherein the reaction is carried out with an aqueous solution of ammonia, at from 20° to 200° C. and from 1 to 20 bars, in the presence of phenol-4-sulfonic acid.

2. A process as claimed in claim 1, wherein the 4-amino-5-chloro-1-phenylpyridaz-6-one is separated from the reaction mixture after the reaction, and the remaining mother liquor is, if desired after the addition of ammonia, aqueous ammonia solution or phenol-4-sulfonic acid, employed again for reaction with further 4,5-dichloro-1-phenylpyridaz-6-one.

* * * * *